United States Patent [19]

Fikes

[11] Patent Number: 4,911,724
[45] Date of Patent: Mar. 27, 1990

[54] ENERGY RESPONSIVE PROSTHETIC LEG
[75] Inventor: Ray Fikes, Lubbock, Tex.
[73] Assignee: J&J Orthotics Inc., Lubbock, Tex.
[21] Appl. No.: 224,167
[22] Filed: Jul. 26, 1988
[51] Int. Cl.⁴ .............................................. A61F 2/80
[52] U.S. Cl. ........................................ 623/37; 623/56
[58] Field of Search .................................. 623/33–37, 623/53–56

[56] References Cited

U.S. PATENT DOCUMENTS

| 951,989 | 3/1910 | Hauger | 623/56 |
|---|---|---|---|
| 2,634,424 | 9/1953 | O'Govman | 623/37 |
| 3,889,301 | 6/1975 | Bonner | 623/37 |
| 4,432,101 | 2/1984 | Johnson | 623/37 |
| 4,655,779 | 4/1987 | Janowiah | 623/37 |

Primary Examiner—Richard J. Apley
Assistant Examiner—James Prizant
Attorney, Agent, or Firm—Richard C. Litman

[57] ABSTRACT

A prosthetic leg component substantially encompasses the tibia or shin portion of the leg and is removably attached to any one of several available prefabricated prosthetic foot devices. Included is a substantially L-shaped member providing for efficient kinetic recoil energy about the ankle upon application of a given load on the device which allows for torsional replication about the tibia while simultaneously providing medial-lateral stability for the user.

2 Claims, 4 Drawing Sheets

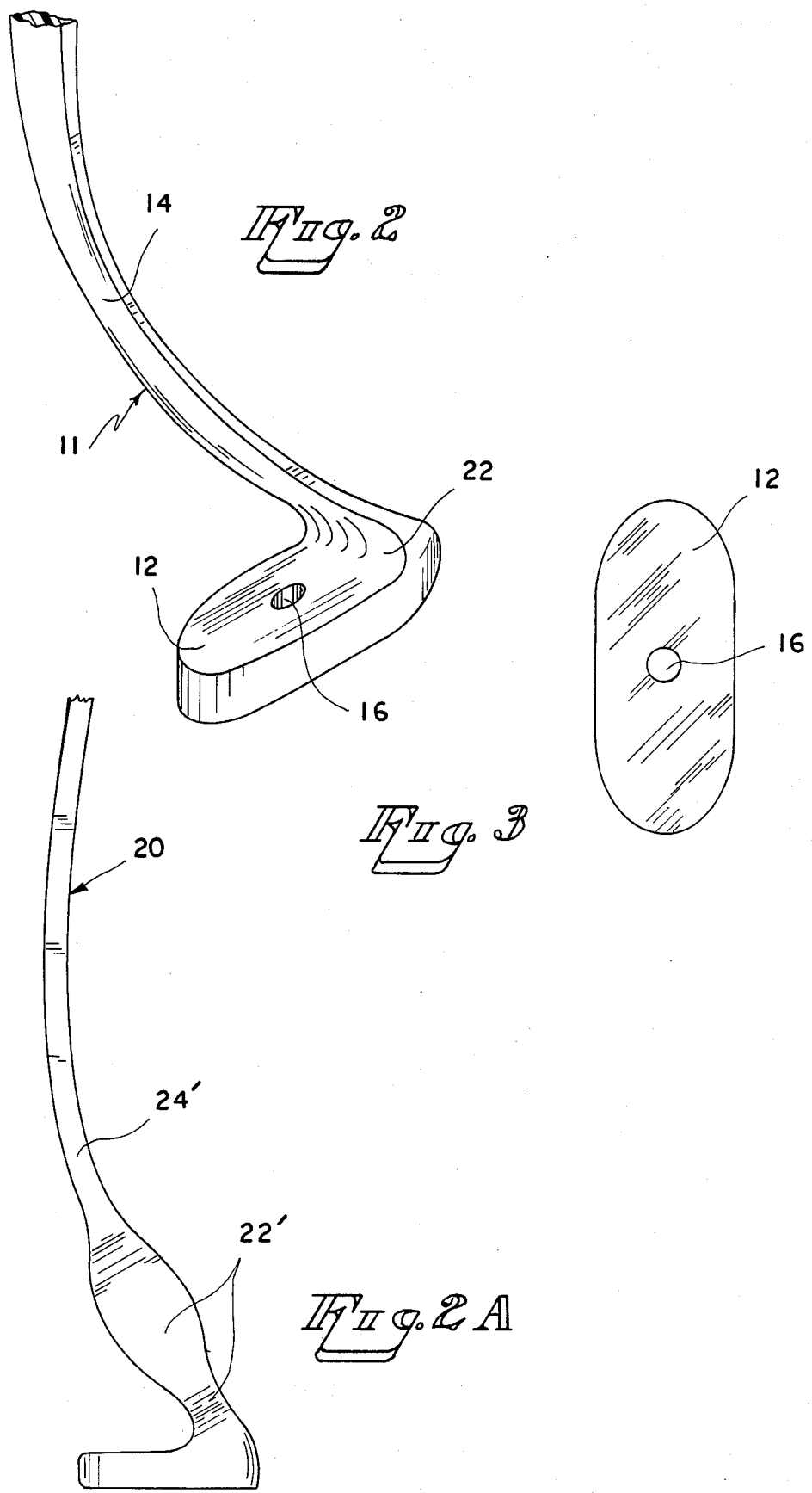

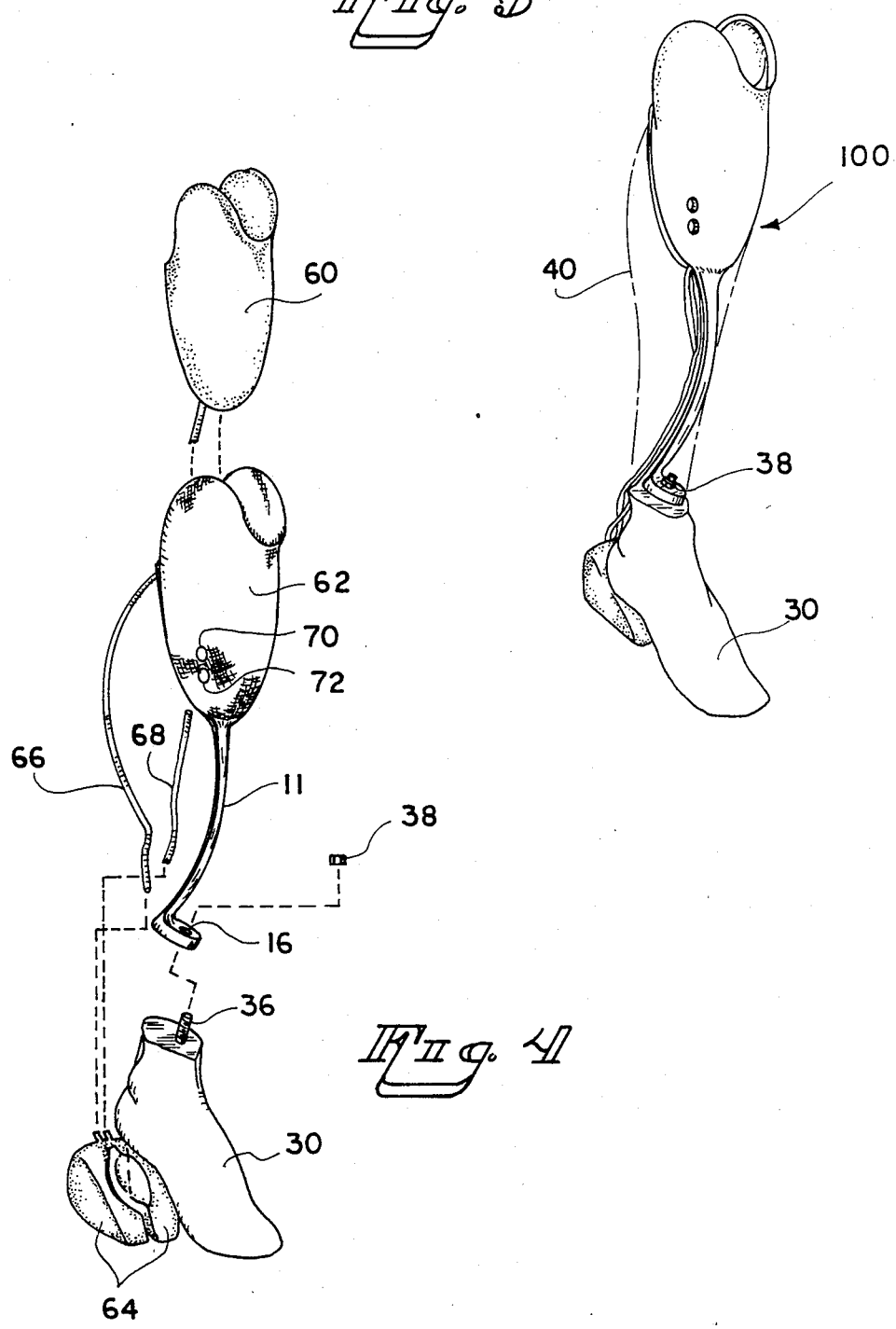

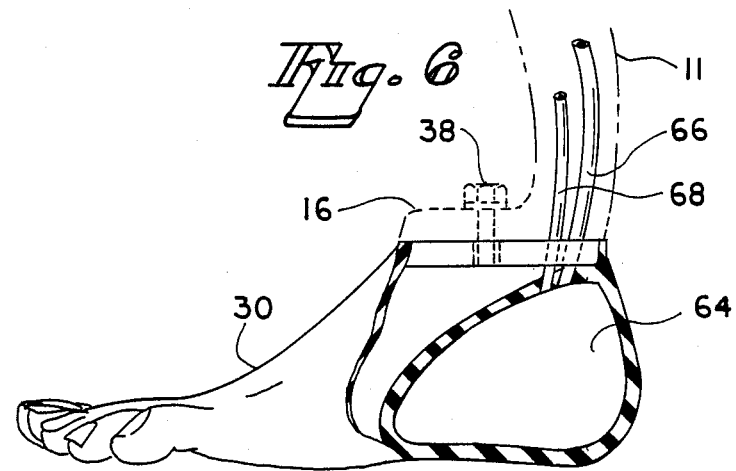

ENERGY RESPONSIVE PROSTHETIC LEG

BACKGROUND OF THE INVENTION

FIELD OF THE INVENTION

This invention relates to prosthetic devices or artificial limbs, and more particularly, to a device for use either by below-knee or above-knee amputees.

The typical or normal walking cycle includes two phases: (a) stance or weight bearing phase and (b) swing phase. Stance phase initiates the instant the heel contacts the ground and terminates when the toes push off the ground (toe-off). Swing phase initiates at toe-off and terminates at heel contact.

It has been noted in prior art leg prosthesis that complete prosthetic restoration of normal functioning during "push-off" is difficult, if not impossible. A proprioceptive sense of knee position is necessary, as well as an active or responsive source of energy in the ankle.

The present invention will be understood to be directed toward a prosthetic leg which is inexpensive in construction and which may be removably secured to any one of a multiplicity of available prosthetic foot devices and whereby, upon placing a load thereon, initiates moments about the knee and ankle, respectively, to transform those respective moments and provide for an active source of energy about the ankle.

The method and construction of the invention is more fully described herein.

DESCRIPTION OF THE PRIOR ART

Various prior art leg prosthesis and the like, as well as the method of their construction in general, are known and are found to be exemplary of the U.S. prior art. They are:

| U.S. Pat. No. | Inventor |
| --- | --- |
| 4,547,913 | Phillips |
| 4,463,459 | Shorter et al. |
| 4,461,045 | Shorter et al. |

U.S. Pat. No. 4,547,913 issued to V. L. Phillips discloses a composite leg and foot prosthetic device which utilizes a resin impregnated high strength filament structure for the leg portion, foot portion, and heel portion, all three of which are rigidly joined at the ankle.

U.S. Pat. No. 4,463,459 issued to J. J. Shorter et al. discloses an artificial leg having a ball and socket ankle joint connected together and clamped over the ball by a turnbuckle ring.

U.S. Pat. No. 4,461,045 also issued to J. J. Shorter et al. discloses an artificial leg which is seen to provide relatively more resistance to dorsi-flexion than to plantar-flexion.

These patents, or known prior art uses, teach and disclose various types of prosthetic devices of sorts and of various manufactures, and the like, as well as methods of their construction; but none of them, whether taken singly or in combination, disclose the specific details of the combination of the invention in such a way as to bear upon the claims of the present invention. More specifically, none of the prior art inventions disclose a prosthetic leg which is selectively attachable to any one of a variety of prefabricated artificial foot members, and furthermore provides for an active source of energy about the ankle. This active source of energy, provided for in the present invention, allows for simulation of normal gait and improved prosthetic restoration relative to the "Push-off" phase of the walking cycle.

SUMMARY OF THE INVENTION

An object of the present invention is to provide for a leg prosthesis which is safe in use and which is selectively attachable to any one of a number of available prefabricated artificial foot members, e.g., prosthetic foot devices having energy responsive elements (springs) therein.

Another object of the present invention is to provide for a prosthetic leg which initiates moments about the knee and ankle portions and transforms these moments into an active source of energy about the ankle.

A further object of the present invention is to provide for a prosthetic leg which simulates the properties involved in the two stages of the normal walking cycle, i.e., stance phase through swing phase.

Another object of the disclosed invention is to provide for a prosthetic device which simulates the interaction between the knee and ankle, respectively, of a normal leg during a normal walking cycle.

A still further object of the present invention is to provide for a complete prosthetic system which will decrease the amount of stress on the traumatized area, thereby providing for long term prosthetic rehabilitation.

Another object of the present invention is to provide for a prosthesis which is psychologically as well as physiologically acceptable to the user.

With these and other objects in view which will more readily appear as the nature of the invention is better understood, the invention consists in the novel construction, combination and arrangement of parts hereinafter more fully described, illustrated and claimed, with reference being made to the appended drawings.

BRIEF DESCRIPTION OF THE DRAWINGS

FIG. 2 is a partial front perspective view of the substantially L-shaped member of the present invention.

FIG. 2A is a side elevation view a second embodiment of the L-shaped member, wherein the ankle is illustrated as being essentially disposed in perpendicular relationship to the shin member of the device.

FIG. 3 is a bottom view of the device shown in FIG. 2, and illustrates an elliptic base member and pin receiving bore for fastening the device to the artificial foot member.

FIG. 4 is an exploded view of a composite energy responsive prosthetic leg illustrating the variable pressurized air regulating members of the present invention.

FIG. 5 is a perspective view of the device seen in FIG. 4, wherein the composite system is shown assembled form and includes a skin tone covering, e.g., foam rubber latex, illustrated in phantom lines.

FIG. 6 is a view of the bellows mounted inside the heel of an artificial foot.

DESCRIPTION OF THE PREFERRED EMBODIMENT

Figure 1:
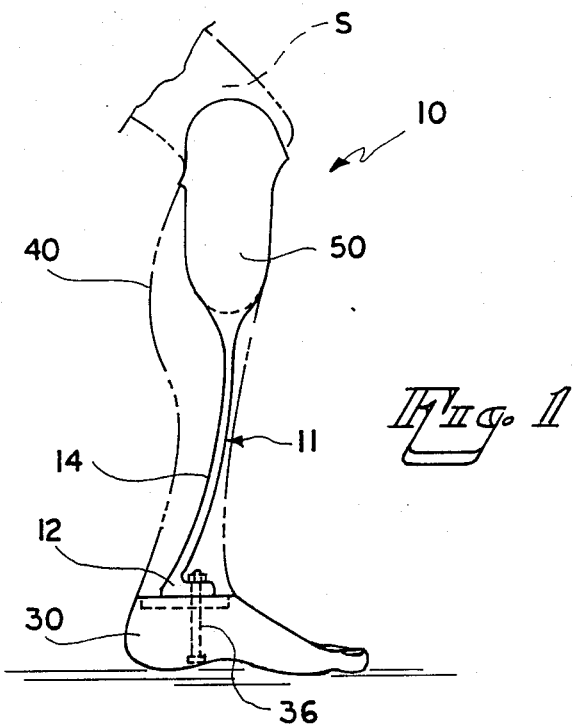
FIG. 1 is a side elevation view of the apparatus as seen attached to a stump receiving member or socket at one end and attached to an artificial foot member at the opposite end.

Referring now to the drawings, wherein like numerals refer to like parts, there is seen in FIGS. 1 and 2 the prosthetic leg 10, including a substantially L-shaped resilient member 11 rigidly affixed to a stump receiving member or socket 50, at one end thereof, and removably attached to an artificial foot member 30 at the opposite lower end thereof.

Figure 1A:
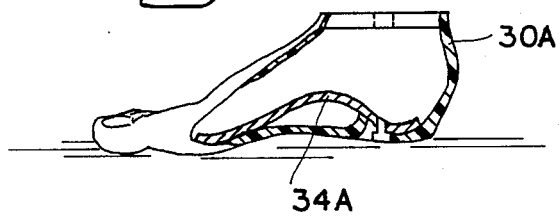
FIGS. 1A and 1B are side elevation views (with portions cut away to illustrate the interior spring mechanisms) of disparate artificial foot members which may be used in conjunction with the present invention.
Figure 1B:
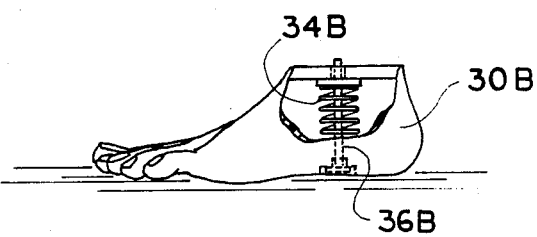

A distinct advantage, as more fully described below, of the prosthetic leg 10 lies in its interchangeable capabilities with respect to currently available artificial foot members, such as foot member 30. The prosthetic foot devices available in today's prosthesis environment are seen to include fastening means, such as pin member 36, wherein the foot members 30 are readily attached to, and removed from, the residual ankle area. The present invention complements this technology by providing for user selective attachment of a multiplicity of artificial foot members. As seen in FIGS. 1A and 1B, disparate artificial or prosthetic foot members, such as foot members 30, 30A, and 30B, are illustrated which have different spring coefficients. FIG. 1A illustrates an artificial foot member 30A which includes a horizontally disposed leaf spring-type mechanism 34A, while the device of FIG. 1B illustrates a foot member 30B including a vertically disposed helical spring mechanism 34B. Either may be selectively provided, or chosen, in accordance to each amputee's physical needs and capabilities. For example, a patient experiencing difficulty during the "push-off" phase of the walking cycle, may require additional reactive loads substantially spanning the lower plane of the "foot", in which case, a device such as that shown in FIG. 1A would produce the desired effect, while the user simulates conventional walking procedure.

Referring now to FIG. 2, the device 10 includes a substantially L-shaped shin member 11 including a resilient vertical member 14 integral with a lower ankle portion 22 in turn joined to an elliptic base member 12. A bore 16 is provided so that, as previously mentioned, a multiplicity of readily available artificial foot members, e.g., helical spring type 30B, may be selectively and removably affixed to the L-shaped shin member 11. Pin member 36 is also provided, and is seen to substantially extend from, and pass through, the lower portion of the prosthetic foot 30. The pin member and foot will be seen to be secured to the shin member 11 by conventional fastening means, such as nut member 38.

Alternately, a second embodiment of the L-shaped member 20 is shown in FIG. 2A and includes an ankle portion 22' essentially disposed in perpendicular relationship to the resilient shin member 24'. Herein, the L-shaped member 20 is seen to provide controlled medial-lateral flexion of the prosthetic leg 20 upon applying a load thereon during use of same. In each L-shaped member embodiment, the shin member 14, 24', will be understood to comprise a transversely disposed flat, blade member.

The geometric shape and recoil properties provided by the device 10 are essential for the two stages of the walking cycle, i.e., stance phase and swing phase. The device is seen to simulate both "push-off" and forward propulsion at the end of the midstance phase. Furthermore, dorsiflexion is important in preventing toe drag after "push-off" and thus requires approximately 15–20 degrees reflection angle with respect to the shin in order to provide substantial kinetic energy about the ankle, thereby initiating the required angular movements in the succeeding swing phase.

The acute angle formed between the lower portion of the vertical member 14, 24' and the elliptical base member 12 provide for an active source of energy in the ankle portion 22 of the L-shaped member 11, 20 during the walking cycle. Herein, upon placing a load on the prosthetic member, the device 10 allows for intiation of knee flexion and assists in the swing phase of the cycle. It should be emphasized here that complete prosthetic restoration in "push-off" phase is difficult to obtain. In prior art inventions an active source of energy about the ankle was not provided for. The present invention alleviates this lack of active energy by initiating moments about the knee and ankle, and also by geometrically providing for an energy responsive system, originating at the residual stump S and terminating about ankle portion 22 of the device, thus greatly enhancing the prosthetic restoration relative to the "push-off" phase of the walking cycle as the user's weight is cyclically applied to the shin member.

Another function provided by the L-shaped member 11 of the present invention 10 is to simulate the interaction between the knee and ankle of the normal leg, wherein the two combine to provide for fluent absorption of the shock caused by heel contact and also to maintain a continuous path relating to the body's center of gravity during this heel-contact phase.

As seen in FIGS. 4 and 5, the present invention further discloses a composite energy responsive prosthetic leg 100, including user variable pressurized air members or bellows 64. Herein, socket member 62 is provided along with a disparate inner bladder 60. The bladder 60 is disposed between socket 62 and the residual stump S of the amputee. The bladder 60 acts as a socket liner. Its variable volume allows for a comfortable, adjustable fit for the stump. Prior to the use of this variable volume air bladder 60, stump socks of single, triple and 5-ply nature were used to adjust the fit between the socket 62 and the stump of the patient's leg. The atrophy of the stump over time would require the addition of more stump socks. The bladder 60 provides a variable size adjustment means. The bellows 64 as seen in FIG. 4, may be displaced adjacent the heel portion of the prosthetic foot 30, or alternately, may be incorporated therein as shown in FIG. 6 (working in conjunction with the S.A.C.H.—Soft Ankle Cushioned Heel—of available prosthetic foot devices). An expansion conduit 66 and contraction conduit 68 provide for the supply and release of pressurized air between the pliable bladder 60 and dual-bellows members 64. This may be accomplished via user regulated expansion valve 70 and user regulated contraction valve 72, respectively, both of which are disposed in readily accessible user areas, such as the medial-lateral portion of socket member 62 of the apparatus. The user can pump up the bladder 60 by opening expansion valve 70 and striking the heel of the prosthetic foot 30 against the bellows 64 to pump up the bladder to a desired fit. Closing valve 70 maintains the pressure fit. Opening valve 72 will reduce the bladder 60 size by releasing air.

Upon complete assembly of the composite energy responsive prosthetic leg 100, as illustrated in FIG. 5, the device allows not only for the dynamic and geometric attributes proposed earlier, i.e., efficient initial loading moments, posterior plantar flexion and dorsiflexion, increased and much desired medial lateral stability, along with an active source of energy about the ankle portion, but also provides for decreased stress on the traumatized area, which is required in a for long term prosthesis.

The cosmetic value of prefabricated prosthetic feet, along with the advent of skin-toned foam rubber latex covering allow for a prosthesis which is natural looking, and therefore psychologically as well as physiologically acceptable to the user.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications, and equivalents which may be resorted to, fall within the scope of the invention.

What is claimed is:

1. A composite energy responsive prosthetic leg comprising:
    a stump retaining socket member;
    a pliable bladder member housed within said stump retaining socket, said pliable bladder including means for selectively controlling pressurized air therein;
    a substantially L-shaped member adapted for connection to an artificial foot member at one end thereof, and also adapted for connection to said stump retaining socket at the opposite end thereof and providing for an active source of energy to said prosthesis about the ankle member thereof;
    bellows means removably provided adjacent said artificial foot member, said bellows means including expansion and contraction means therein, said bellows further being pneumatically connected via conduits to said pliable bladder and providing pressurized air thereto upon contraction of said bellows;
    whereby said pressurized air within said pliable bladder member provides support means and suspension regulating means for said stump within said stump retaining socket during suspension of same, and whereby said L-shaped member provides for an active source of energy in the ankle portion of the prosthetic leg, thus allowing for substantially normal gait during the use thereof.

2. A composite energy responsive leg of claim 1 wherein,
    said bellows are disposed within said artificial foot member.

* * * * *